US012400362B2

United States Patent
Ong et al.

(10) Patent No.: US 12,400,362 B2
(45) Date of Patent: Aug. 26, 2025

(54) MEDICAL IMAGE PROCESSING DEVICE, ULTRASONIC DIAGNOSTIC DEVICE, AND STORAGE MEDIUM

(71) Applicant: CANON MEDICAL SYSTEMS CORPORATION, Otawara (JP)

(72) Inventors: Guang Yi Ong, Nasushiobara (JP); Atsuko Sugiyama, Nasushiobara (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 482 days.

(21) Appl. No.: 17/806,112

(22) Filed: Jun. 9, 2022

(65) Prior Publication Data

US 2022/0405963 A1 Dec. 22, 2022

(30) Foreign Application Priority Data

Jun. 17, 2021 (JP) ................................ 2021-101074

(51) Int. Cl.
*A61B 8/08* (2006.01)
*A61B 8/00* (2006.01)
(Continued)

(52) U.S. Cl.
CPC .............. *G06T 7/74* (2017.01); *A61B 8/0825* (2013.01); *A61B 8/469* (2013.01); *A61B 8/5223* (2013.01);
(Continued)

(58) Field of Classification Search
CPC ..................... G06T 7/74; G06T 7/0012; G06T 2207/10132; G06T 2207/30068;
(Continued)

(56) References Cited

U.S. PATENT DOCUMENTS

2012/0020536 A1\* 1/2012 Moehrle ............... G06T 7/0014
382/128
2014/0056502 A1\* 2/2014 Twellmann ........... G06T 7/0012
382/131
(Continued)

FOREIGN PATENT DOCUMENTS

JP 2014-14469 A 1/2014
JP 2015-27450 A 2/2015
(Continued)

OTHER PUBLICATIONS

Japanese Office Action issued Oct. 29, 2024 in Japanese Patent Application No. 2021-101074, citing documents 15-19 therein, 7 pages.

*Primary Examiner* — Henok Shiferaw
*Assistant Examiner* — Dion J Satcher
(74) *Attorney, Agent, or Firm* — Oblon, McClelland, Maier & Neustadt, L.L.P.

(57) ABSTRACT

A medical image processing device of an embodiment has processing circuitry. The processing circuitry performs position transformation to represent a position in a region of interest set in a captured mammography image of a breast of a subject and an examination position on a body of the subject in an ultrasound examination in a plane of the same scale, determines whether or not the position in the region of interest and the examination position match in the plane, and saves or outputs an ultrasonic image corresponding to the examination position upon determining that the position in the region of interest matches the examination position.

15 Claims, 14 Drawing Sheets

(51) Int. Cl.
*G06T 7/00* (2017.01)
*G06T 7/73* (2017.01)

(52) U.S. Cl.
CPC .......... *A61B 8/5246* (2013.01); *G06T 7/0012* (2013.01); *G06T 2207/10132* (2013.01); *G06T 2207/30068* (2013.01); *G06T 2207/30096* (2013.01)

(58) Field of Classification Search
CPC ............. G06T 2207/30096; G06T 7/33; G06T 2207/10116; A61B 8/0825; A61B 8/469; A61B 8/5223; A61B 8/5246
See application file for complete search history.

(56) References Cited

U.S. PATENT DOCUMENTS

| | | | |
|---|---|---|---|
| 2016/0155227 A1* | 6/2016 | Chae | A61B 8/5223 |
| | | | 382/131 |
| 2016/0314587 A1* | 10/2016 | Ishikawa | G16H 50/20 |
| 2017/0086785 A1* | 3/2017 | Bjaerum | A61B 8/4444 |
| 2018/0220994 A1* | 8/2018 | Sugiyama | A61B 6/464 |
| 2019/0251327 A1* | 8/2019 | Laviola | A61B 8/5261 |
| 2019/0325573 A1* | 10/2019 | Bernard | A61B 8/085 |
| 2020/0305821 A1* | 10/2020 | Sendai | A61B 6/025 |
| 2020/0323512 A1* | 10/2020 | Ng | A61B 8/085 |

FOREIGN PATENT DOCUMENTS

| | | |
|---|---|---|
| JP | 2015-100661 A | 6/2015 |
| JP | 2018-126204 A | 8/2018 |
| JP | 2019-193788 A | 11/2019 |
| JP | 2020-157056 A | 10/2020 |

\* cited by examiner

MEDICAL IMAGE PROCESSING DEVICE,
ULTRASONIC DIAGNOSTIC DEVICE, AND
STORAGE MEDIUM

CROSS-REFERENCE TO RELATED
APPLICATION

The present application claims priority based on Japanese Patent Application No. 2021-101074 filed on Jun. 17, 2021, the content of which is incorporated herein by reference.

FIELD

Embodiments disclosed in the present specification and drawings relate to a medical image processing device, an ultrasonic diagnostic device, and a storage medium.

BACKGROUND

In recent years, in the field of medical image diagnosis, diagnosis has been performed on subjects by making a comprehensive decision with medical images obtained from various imaging devices. For example, a diagnostic method is used in which a primary examination for examining the presence or absence of a lesion in a subject is performed using a first imaging device (for example, a mammography device) and further a secondary examination for examining the conditions of the lesion site in detail is performed using a second imaging device (for example, an ultrasonic diagnostic device) if the presence of a lesion is suspected.

In such a secondary examination, a technician, a doctor, or the like who operates the second imaging device needs to, while visually checking the result of the primary examination, manually operate the second imaging device and align the imaging range with the lesion site to perform the imaging process. Thus, it takes labor to operate the second imaging device and it takes time for examination.

DETAILED DESCRIPTION

Hereinafter, a medical image processing device, an ultrasonic diagnostic device, and a storage medium will be described with reference to the drawings.

A medical image processing device of an embodiment includes processing circuitry. The processing circuitry performs position transformation to represent a position in a region of interest set in a captured mammography image of a breast of a subject and an examination position on a body of the subject in an ultrasound examination in a plane of the same scale, determines whether or not the position in the region of interest and the examination position matches in the plane and saves or outputs an ultrasonic image corresponding to the examination position upon determining that the position in the region of interest matches the examination position.

First Embodiment

Configuration of Ultrasonic Diagnostic Device

Figure 1:
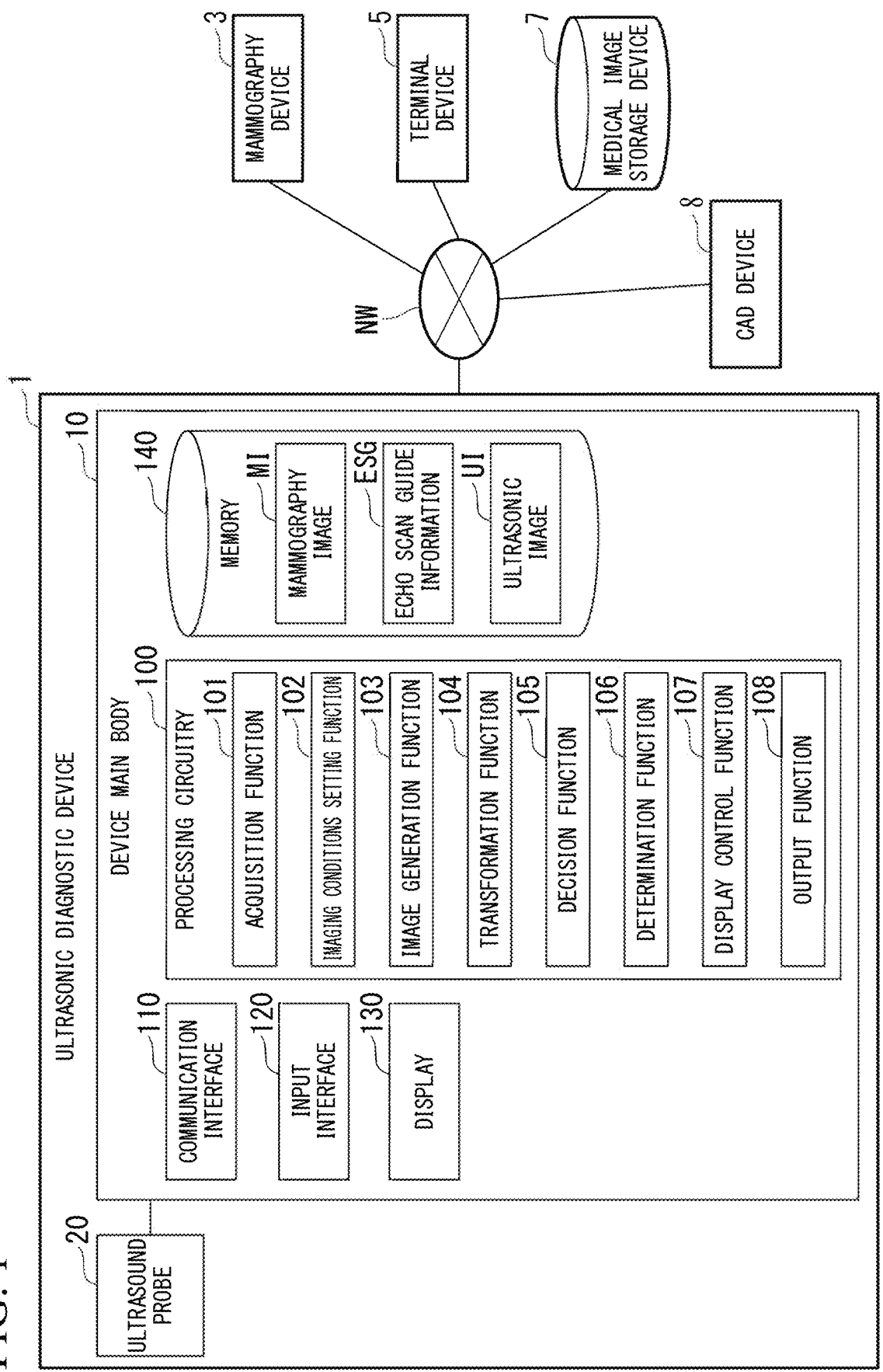
FIG. 1 is a block diagram showing an exemplary configuration of an ultrasonic diagnostic device 1 according to a first embodiment.

FIG. 1 is a block diagram showing an exemplary configuration of an ultrasonic diagnostic device 1 according to the first embodiment. The ultrasonic diagnostic device 1 is disposed, for example, in a medical institution such as a hospital. The ultrasonic diagnostic device 1 is operated, for example, by an operator such as a technician or a doctor and captures an internal medical image of the body of a subject who is a patient. The ultrasonic diagnostic device 1 is connected, for example, to a mammography device 3, a terminal device 5, a medical image storage device 7, and a computer-aided diagnosis/detection (CAD) device 8 via a communication network NW such that the ultrasonic diagnostic device 1 can transmit and receive data to and from each of them. The ultrasonic diagnostic device 1 is an example of a "medical image processing device" or an "ultrasonic diagnostic device." The CAD device 8 is an example of the "medical image processing device." The mammography device 3 and the medical image storage device 7 are examples of an "external device."

The communication network NW refers to any information communication network that uses telecommunications technology. The communication network NW includes a wireless/wired local area network (LAN) such as a hospital backbone LAN and the Internet as well as a telephone communication line network, an optical fiber communication network, a cable communication network, a satellite communication network, and the like.

The mammography device 3 irradiates a breast of a subject with X-rays, detects X-rays that have passed through the breast, and generates a mammography image. The mammography device 3 transmits the generated mammography image to the ultrasonic diagnostic device 1, the terminal device 5, the medical image storage device 7, the CAD device 8, and the like via the communication network NW.

The terminal device 5 displays, for example, an ultrasonic image received from the ultrasonic diagnostic device 1, a mammography image received from the mammography device 3, and an ultrasonic image and a mammography image acquired from the medical image storage device 7. The terminal device 5 is operated, for example, by a doctor who makes a diagnosis using a medical image such as an ultrasonic image or a mammography image.

The medical image storage device 7 stores medical images such as an ultrasonic image received from the ultrasonic diagnostic device 1 and a mammography image received from the mammography device 3 in association with subject information, imaging conditions, and the like.

The CAD device 8 is a mammography CAD device that supports a mammography examination, an ultrasonic CAD device that supports an ultrasound examination, or the like. For example, the mammography CAD device automatically detects a site where a lesion is suspected in a mammography image and sets a region of interest including the detected site. For example, the ultrasonic CAD device automatically detects a site where a lesion is suspected from an ultrasonic image. The functions of the CAD device 8 may be incorporated into the ultrasonic diagnostic device 1.

The ultrasonic diagnostic device 1 includes, for example, a device main body 10 and an ultrasound probe 20. The ultrasound probe 20 is operated, for example, by an operator and is pressed against part of a subject (the part to be examined or diagnosed). For example, the ultrasound probe 20 transmits (emits) an ultrasonic wave to the subject to acquire an internal image of the subject. The ultrasound probe 20 receives echoes (reflected waves) of the transmitted ultrasonic wave. Then, the ultrasound probe 20 generates signal data of the received echoes (hereinafter referred to as "echo data") and outputs the echo data to the device main body 10.

The device main body 10 includes, for example, processing circuitry 100, a communication interface 110, an input interface 120, a display 130, and a memory 140. The communication interface 110 communicates with an external device such as the terminal device 5 via the communication network NW. The communication interface 110 includes, for example, a communication interface such as a network interface card (NIC).

The input interface 120 receives various input operations from the operator of the ultrasonic diagnostic device 1, converts the received input operations into electric signals and outputs the electric signals to the processing circuitry 100. The input interface 120 includes, for example, a mouse, a keyboard, a trackball, a switch, a button, a joystick, and a touch panel. The input interface 120 may be, for example, a user interface that receives voice input such as a microphone.

In the present specification, the input interface is not limited to those provided with physical operating parts such as a mouse and a keyboard. Examples of the input interface also include, for example, electric signal processing circuitry that receives an electric signal corresponding to an input operation from an external input device provided separately from the ultrasonic diagnostic device and outputs the electric signal to a control circuit.

The display 130 displays various information. The display 130 displays, for example, an image generated by the processing circuitry 100 and a graphical user interface (GUI) for receiving various input operations from the operator. The display 130 is, for example, a liquid crystal display (LCD), a cathode ray tube (CRT) display, or an organic electro-luminescence (EL) display. When the input interface 120 is a touch panel, the display function of the display 130 may be incorporated into the input interface 120.

The processing circuitry 100 includes, for example, an acquisition function 101, an imaging conditions setting function 102, an image generation function 103, a transformation function 104, a decision function 105, a determination function 106, a display control function 107, and an output function 108. The processing circuitry 100 implements these functions, for example, by a hardware processor (computer) executing a program stored in a memory 140 (a storage circuit). The acquisition function 101 is an example of an "acquisition unit." The imaging conditions setting function 102 is an example of an "imaging conditions setting unit." The transformation function 104 is an example of a "transformation unit." The decision function 105 is an example of a "decision unit." The determination function 106 is an example of a "determination unit." The output function 108 is an example of an "output unit." The hardware processor refers to circuitry such as, for example, a central processing unit (CPU), a graphics processing unit (GPU), an application specific integrated circuit (ASIC), or a programmable logic device (for example, a simple programmable logic device (SPLD), a complex programmable logic device (CPLD), or a field programmable gate array (FPGA)). Instead of storing the program in the memory 140, the program may be directly embedded in the circuitry of the hardware processor. In this case, the hardware processor implements the functions by reading and executing the program embedded in the circuitry. The program may be stored in the memory 140 in advance or may be stored in a non-transient storage medium such as a DVD or a CD-ROM and then installed in the memory 140 from the non-transient storage medium by mounting the non-transient storage medium in a drive device (not shown) of the ultrasonic diagnostic device 1. The hardware processor is not limited to that constructed as a single circuit but a plurality of independent circuits may be combined to construct one hardware processor to implement the functions. A plurality of components may also be integrated into one hardware processor to implement the functions.

The acquisition function 101 acquires the echo data output by the ultrasound probe 20. The acquisition function 101 also acquires a mammography image MI, echo scan guide information ESG, and the like from the mammography device 3 and the medical image storage device 7 via the communication interface 110 and stores them in the memory 140.

The echo scan guide information ESG is information indicating a region of interest set for the mammography image MI captured by the mammography device 3. This region of interest includes, for example, a site where a lesion is confirmed or a site where a lesion is suspected (hereinafter also referred to as a "lesion site") in the mammography image MI. This region of interest is set, for example, by a technician, a doctor (a radiologist), or the like, who has performed a mammography examination, before an ultrasound examination is performed after the mammography examination. Alternatively, this region of interest may be automatically set by the mammography CAD device. Such echo scan guide information ESG is used to check the same lesion site as the region of interest (lesion site) indicated by the mammography image MI when performing the ultrasound examination. The echo scan guide information ESG is an example of the "region of interest."

Figure 2:
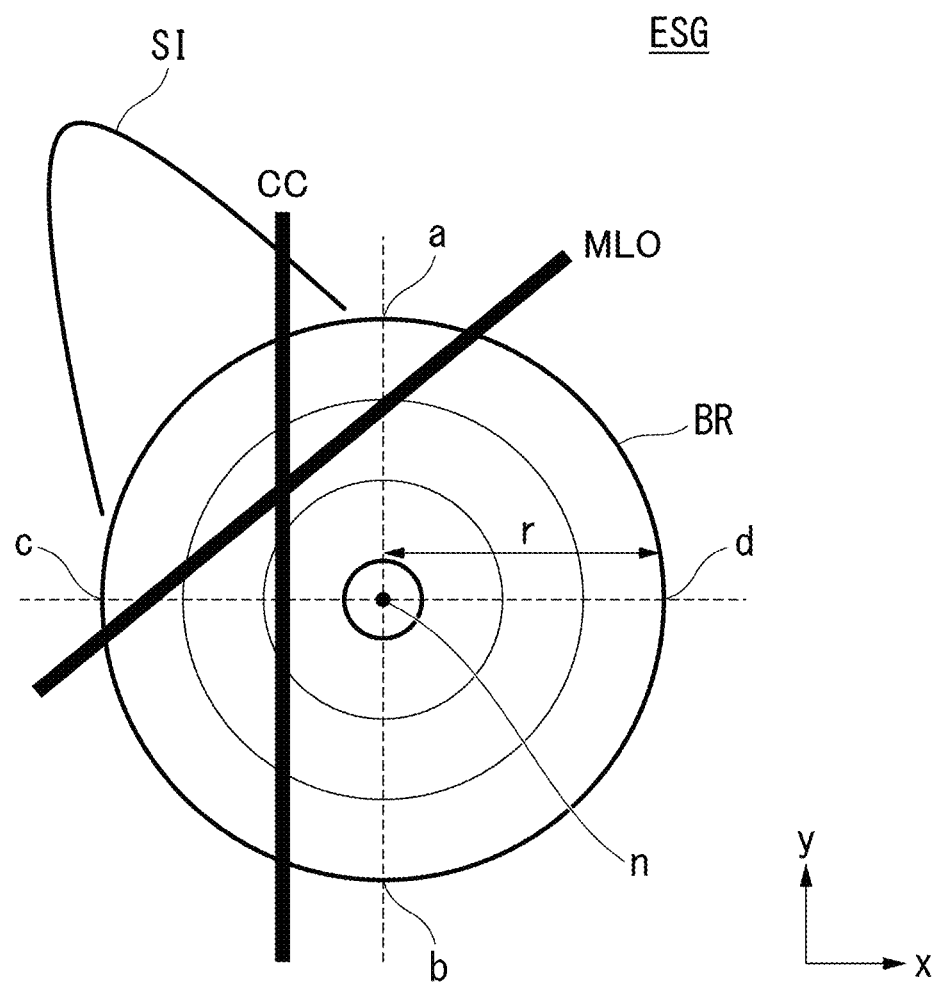
FIG. 2 is a diagram showing an example of echo scan guide information ESG according to the first embodiment.

FIG. 2 is a diagram showing an example of the echo scan guide information ESG according to the first embodiment. The echo scan guide information ESG includes information on the breast BR of the subject such as, for example, the position of the nipple n, a start point and an end point of a mediolateral oblique (MLO) axis, a relative position between the MLO axis and the nipple n, a start point and an end point of a craniocaudal (head-to-tail) (CC) axis, a relative position between the CC axis and the nipple n, an upper end a of the breast, a lower end b of the breast, a right end c of the breast, a left end d of the breast, the angle of a support base of the mammography device 3, and the position of a flank S1. As shown in FIG. 2, the echo scan guide information ESG is displayed on a schematic diagram schematically showing the breast.

That is, the echo scan guide information ESG (the region of interest) includes a first region of interest (the MLO axis) set in a first mammography image of the breast BR captured in a first direction and a second region of interest (the CC axis) set in a second mammography image of the breast BR captured in a second direction.

Figure 3A:
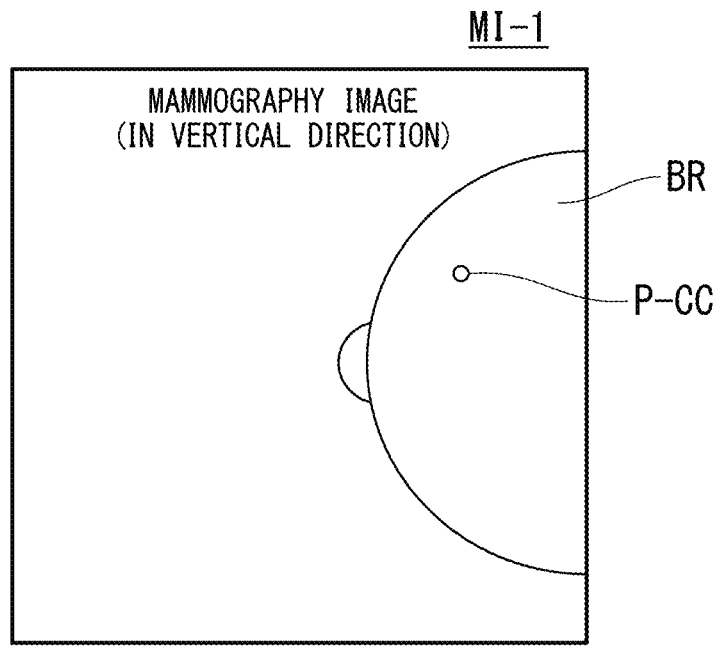
FIG. 3A is a diagram showing how a CC axis is designated for a mammography image according to the first embodiment.
Figure 3B:
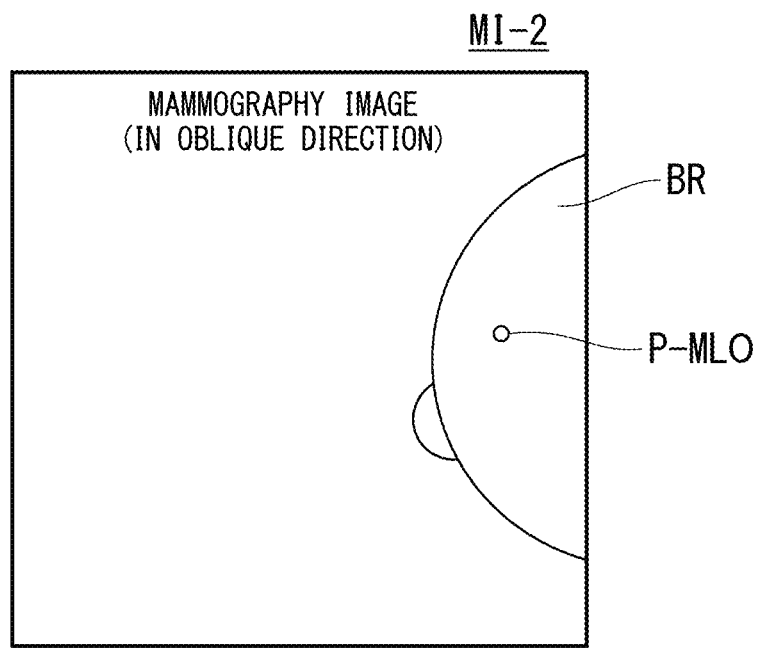
FIG. 3B is a diagram showing how an MLO axis is designated for a mammography image according to the first embodiment.

FIGS. 3A and 3B are diagrams showing how a technician or the like designates a CC axis and an MLO axis for mammography images according to the first embodiment. FIG. 3A is a mammography image MI-1 of the breast BR of the subject captured in a vertical direction. FIG. 3B is a mammography image MI-2 of the breast BR of the subject captured in an oblique direction. For example, the technician or the like who has performed a mammography examination checks the mammography image MI-1 and operates the input interface to designate a point P-CC which is a lesion site. An axis in the craniocaudal direction of the breast BR which passes through the point P-CC thus designated is set as the CC axis in FIG. 2. For example, the technician or the like also checks the mammography image MI-2 and operates the input interface to designate a point P-MLO which is the lesion site. An axis in the mediolateral oblique direction of the breast BR which passes through the point P-MLO thus designated is set as the MLO axis in FIG. 2. Also, only one of the MLO and CC axes may be set.

The imaging conditions setting function 102 sets imaging conditions based on input operations received from the operator via the input interface 120. The imaging conditions include the setting of measurement reference points for identifying the position of the ultrasound probe 20 during an ultrasound examination. Other imaging conditions include various parameters relating to image adjustment. Other imaging conditions also include information such as the type of the ultrasound probe 20 used for imaging and whether or not a stress echo examination is to be performed. That is, the imaging conditions setting function 102 performs setting for identifying an examination position on the body of the subject, which is in contact with the ultrasound probe 20 during an ultrasound examination, based on the position information of predetermined portions on the body of the subject.

The image generation function 103 generates an ultrasonic image UI, which is an image showing an internal shape of the subject, based on the echo data acquired by the acquisition function 101 and stores the ultrasonic image UT in the memory 140.

The transformation function 104 performs coordinate transformation such that coordinates of the echo scan guide information ESG acquired by the acquisition function 101 and coordinates of body mark information automatically set when an ultrasound examination is performed are represented in the same plane coordinates (a plane of the same scale). The body mark information indicates a position on the body of the subject which is in contact with the ultrasound probe 20 during the ultrasound examination. That is, the transformation function 104 performs position transformation such that positions in the region of interest set in the captured mammography image of the breast of the subject and the examination position on the body of the subject in the ultrasound examination are represented in a plane of the same scale. In other words, the transformation function 104 performs position transformation such that a position in the region of interest and the examination position on the body of the subject which is in contact with the ultrasound probe during an ultrasound examination are represented in a plane of the same scale.

Figure 4:
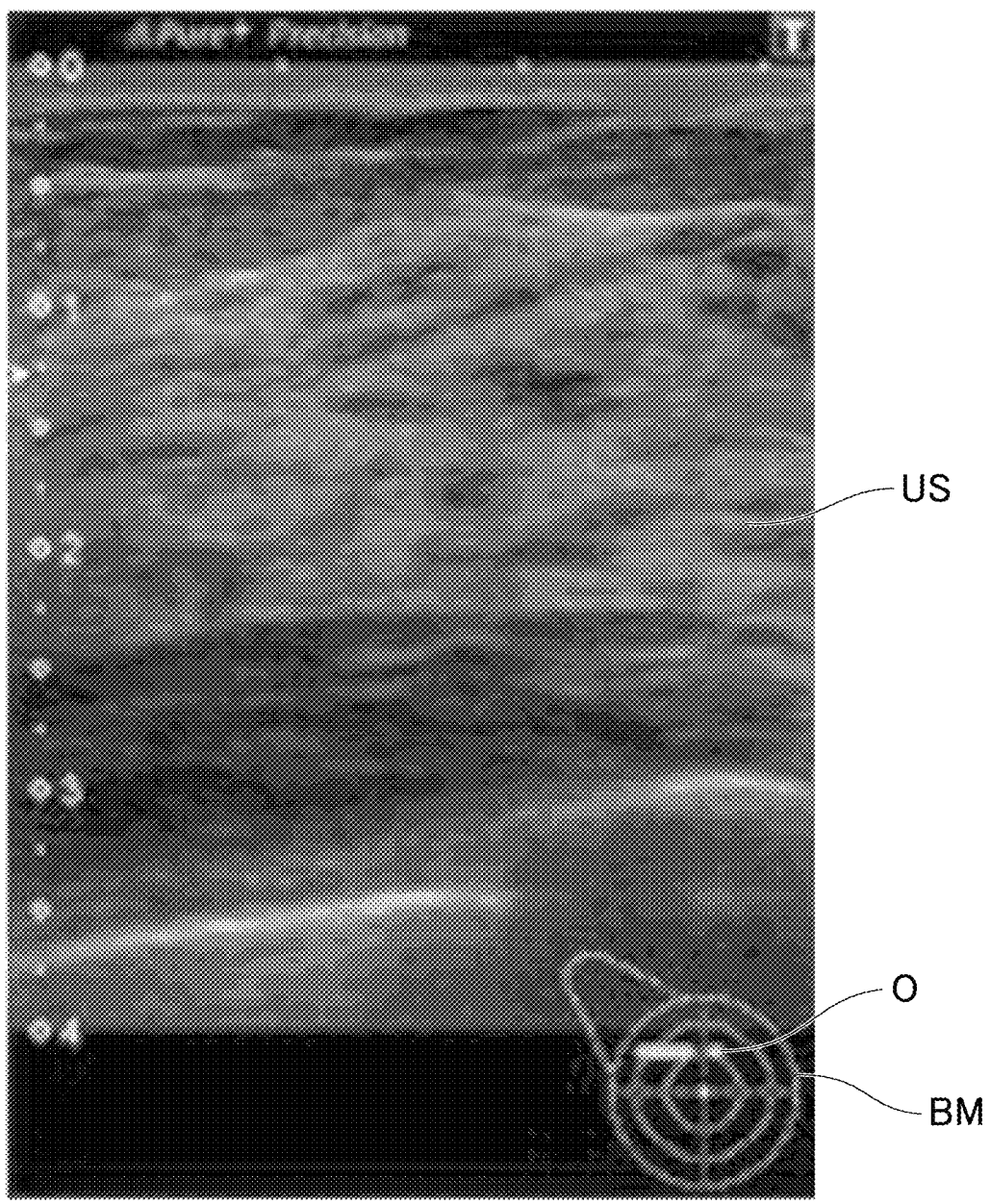
FIG. 4 is a diagram showing an example of an acquisition screen for acquiring an ultrasonic image US according to the first embodiment.
Figure 5:
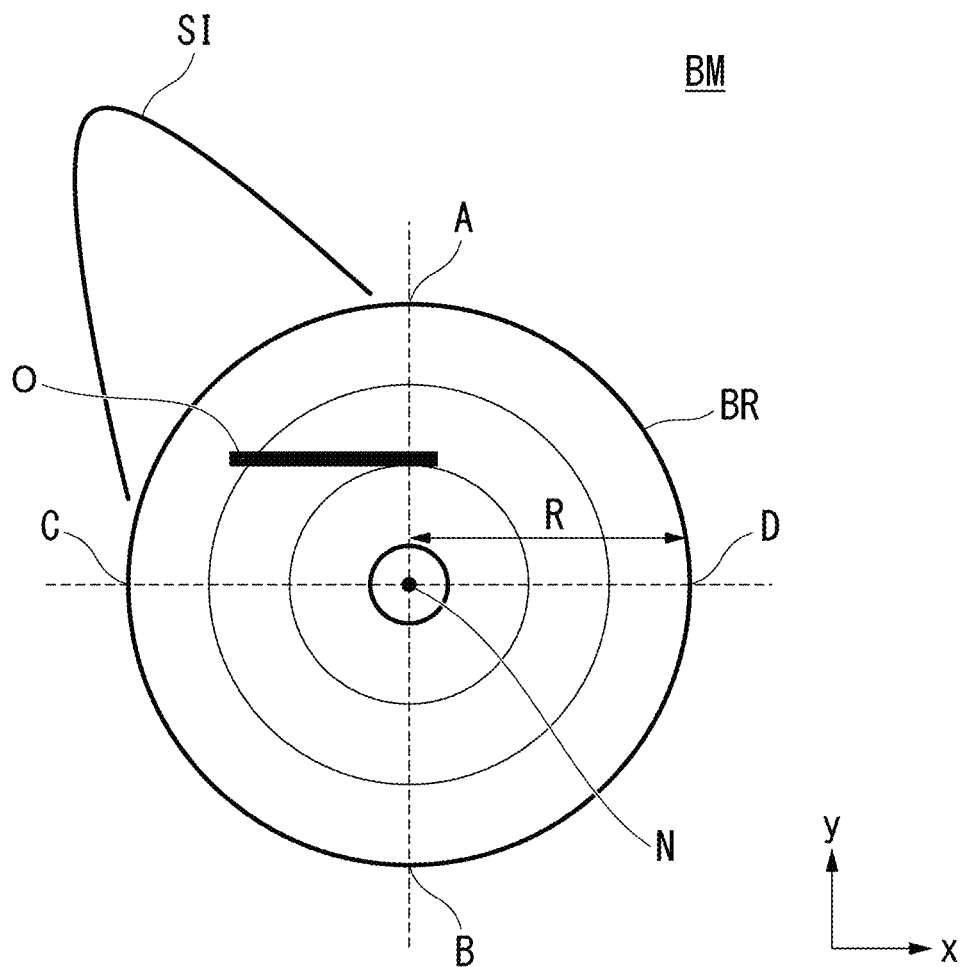
FIG. 5 is a diagram showing an example of body mark information BM according to the first embodiment.

FIG. 4 is a diagram showing an example of an acquisition screen for acquiring an ultrasonic image US according to the first embodiment. FIG. 5 is a diagram showing an example of the body mark information BM according to the first embodiment. As shown in FIG. 4, a body mark BM is displayed on the display 130 in addition to the ultrasonic image US when an ultrasound examination is performed. As shown in FIG. 5, the body mark information BM includes information on the breast BR of the subject such as, for example, the position of the nipple N, an upper end A of the breast, a lower end B of the breast, a right end C of the breast, a left end D of the breast, the position O of the ultrasound probe 20, and a relative position between the position of the ultrasound probe 20 and the position of the nipple N. As shown in FIG. 5, the body mark information BM is displayed on a schematic diagram schematically showing the breast. When the position of the ultrasound probe 20 is represented in the body mark information BM by a line having a predetermined width corresponding to the shape of the ultrasound probe 20, the body mark information BM includes information on a start point and an end point of the line. Rather than being represented by a figure, the body mark information BM may be represented by coordinates indicating the relative position of the ultrasound probe 20 on the subject, which are calculated based on characteristics relating to the body shape of the subject and the like.

The transformation function 104 maps the coordinates of the echo scan guide information ESG to the coordinates of the body mark information BM. Alternatively, the transformation function 104 maps the coordinates of the body mark information BM to the coordinates of the echo scan guide information ESG or maps the coordinates of the echo scan guide information ESG and the coordinates of the body mark information BM to other specific coordinates. Details of the transformation function 104 will be described later.

The decision function 105 decides positions on the body of the subject where an ultrasonic image is to be captured (hereinafter referred to as "imaging positions"), for example, based on input operations received from the operator via the input interface 120. The decision function 105 may also decide the number and locations of imaging positions based on a predetermined guideline. An imaging position is an example of an "acquisition position." That is, the decision function 105 decides acquisition positions of an ultrasonic image within the region of interest. The decision function 105 decides acquisition positions within the first region of interest and the second region of interest. Details of the decision function 105 will be described later.

The determination function 106 determines whether or not the current position (examination position) of the ultrasound probe 20 and a decided imaging position match during an ultrasound examination. Upon determining that the current position of the ultrasound probe 20 and a decided imaging position match, the determination function 106 causes the memory 140 to store an ultrasonic image UI generated by the image generation function 103 in association with subject information, imaging conditions, and the like. That is, the determination function 106 determines whether or not a position in the region of interest and the examination position matches in a plane in which positions in the region of interest set in the mammography image and the examination position on the body of the subject in the ultrasound examination are on the same scale. The determination function 106 determines whether or not a position in the region of interest matches the examination position on the body of the subject which is in contact with the ultrasound probe 20 during an ultrasound examination. Upon determining that a position in the region of interest matches the examination position, the determination function 106 saves or outputs an ultrasonic image corresponding to the examination position.

The display control function 107 performs control such that the display 130 displays various information such as the mammography image MI, the echo scan guide information ESG, the body mark information BM, the ultrasonic image UI, and the GUI for receiving various input operations from the operator.

The output function 108 outputs the ultrasonic image UI stored in the memory 140 to the terminal device 5 or the like via the network NW using the communication interface 110.

The memory 140 is realized, for example, by a random access memory (RAM), a semiconductor memory device such as a flash memory, a hard disk, or an optical disc. These non-transient storage media may also be realized by another storage device connected via the communication network NW such as a network attached storage (NAS) or an external storage server device. The memory 140 may also include a non-transient storage medium such as a read only memory (ROM) or a register. The memory 140 stores, for example, the mammography image MI, the echo scan guide information ESG, and the ultrasonic image UI. In addition, the memory 140 stores programs, parameter data, and other data used by the processing circuitry 100.

Process Flow

Figure 6:
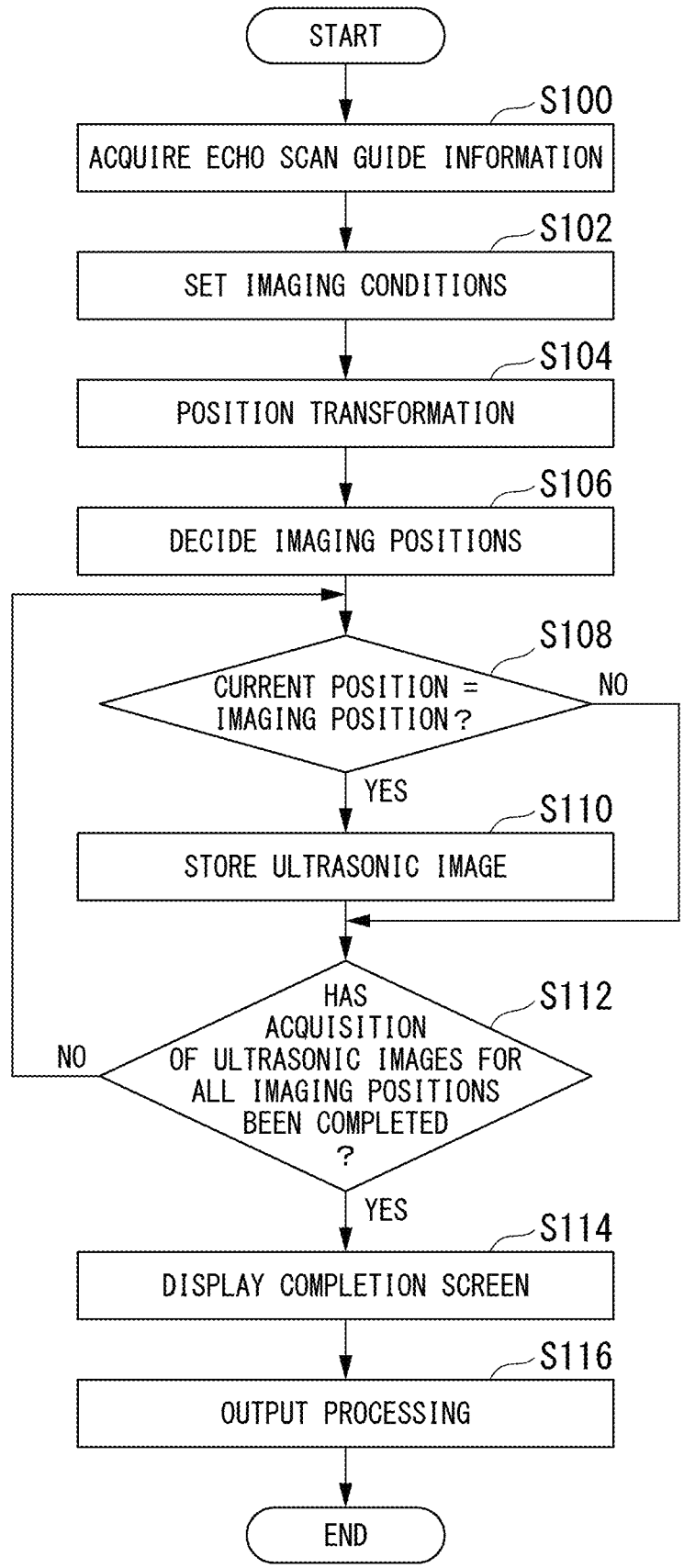
FIG. 6 is a flowchart showing an example of a flow of a process performed by the ultrasonic diagnostic device 1 according to the first embodiment.

Next, an example of a process performed by the ultrasonic diagnostic device 1 will be described. FIG. 6 is a flowchart showing an example of a flow of the process performed by the ultrasonic diagnostic device 1 according to the first embodiment.

First, the acquisition function 101 acquires echo scan guide information ESG from the mammography device 3 or the medical image storage device 7 via the communication interface 110 (step S100).

Next, the imaging conditions setting function 102 sets imaging conditions based on input operations received from the operator via the input interface 120 (step S102). The imaging conditions setting function 102 sets measurement reference points for identifying the position of the ultrasound probe 20 (that is, body mark information BM) during an ultrasound examination. The imaging conditions setting function 102 sets some predetermined portions on the body of the subject as measurement reference points. Generally, body mark information BM corresponding to the position of the ultrasound probe 20 can be calculated by calculating the coordinates of three portions on the subject. In the present embodiment, the coordinates of the position of the nipple in addition to the positions of four points at the top, bottom, left, and right of the breast of the subject are calculated as measurement reference points in consideration of the convenience and accuracy of setting measurement reference points. Specifically, the operator presses the ultrasound probe 20 against each of the positions of the four points at the top, bottom, left, and right of the breast of the subject and the position of the nipple to measure the coordinates of each of the positions and register them as measurement reference points. The position of the nipple does not have to be used as a measurement reference point.

Next, the transformation function 104 performs position transformation such that the coordinates of the echo scan guide information ESG acquired by the acquisition function 101 and the coordinates of the body mark information BM set by the imaging conditions setting function 102 are represented in the same coordinate plane (step S104). For example, the transformation function 104 maps the coordinates of the echo scan guide information ESG to the coordinates of the body mark information BM.

The case where the coordinates of the echo scan guide information ESG shown in FIG. 2 are mapped to the coordinates of the body mark information BM shown in FIG. 5 will be described as an example. First, the transformation function 104 calculates a radius r of the breast BR which is the distance between the position of the nipple n and an end point of the breast on the echo scan guide information ESG shown in FIG. 2. The transformation function 104 calculates the distance between the position of the nipple n and the end point of any one of the upper end a, the lower end b, the right end c, and the left end d as the radius r. For example, when the transformation function 104 uses the distance between the nipple position n and the left end d, the radius r is calculated using the following equation (1).

$$r = n_x - d_x \quad (1)$$

In the above equation (1), the subscript x indicates the x coordinate in the xy spatial coordinate system defined on the echo scan guide information ESG. In this case, the x-axis of the xy spatial coordinate system is in a direction along a line connecting the left end d and the right end c of the breast BR and the y-axis is in a direction along a line connecting the upper end a and the lower end h of the breast BR. The transformation function 104 may calculate the distances between the nipple position n and the points of the upper end a, the lower end b, the right end c, and the left end d and calculate an average of the distances as the radius r.

Next, the transformation function 104 calculates a radius R of the breast BR which is the distance between the position of the nipple N and an end point of the breast on the body mark information BM shown in FIG. 5. The transformation function 104 calculates the distance between the position of the nipple N and the end point of any one of the upper end A, the lower end B, the right end C, and the left end D as the radius R. For example, when the transformation function 104 uses the distance between the nipple position N and the left end D, the radius R is calculated using the following equation (2).

$$R = N_x - D_x \quad (2)$$

In the above equation (2), the subscript x indicates the x coordinate in the xy spatial coordinate system defined on the body mark information BM. In this case, the x-axis of the xy spatial coordinate system is in a direction along a line connecting the left end D and the right end C of the breast BR and the y-axis is in a direction along a line connecting the upper end A and the lower end B of the breast BR. The transformation function 104 may calculate the distances between the nipple position N and the points of the upper end A, the lower end B, the right end C, and the left end D and calculate an average of the distances as the radius R.

Next, the transformation function 104 calculates a ratio k of the radius R on the body mark information BM to the radius r on the echo scan guide information ESG using the following equation (3).

$$k=R/r \quad (3)$$

Figure 7:
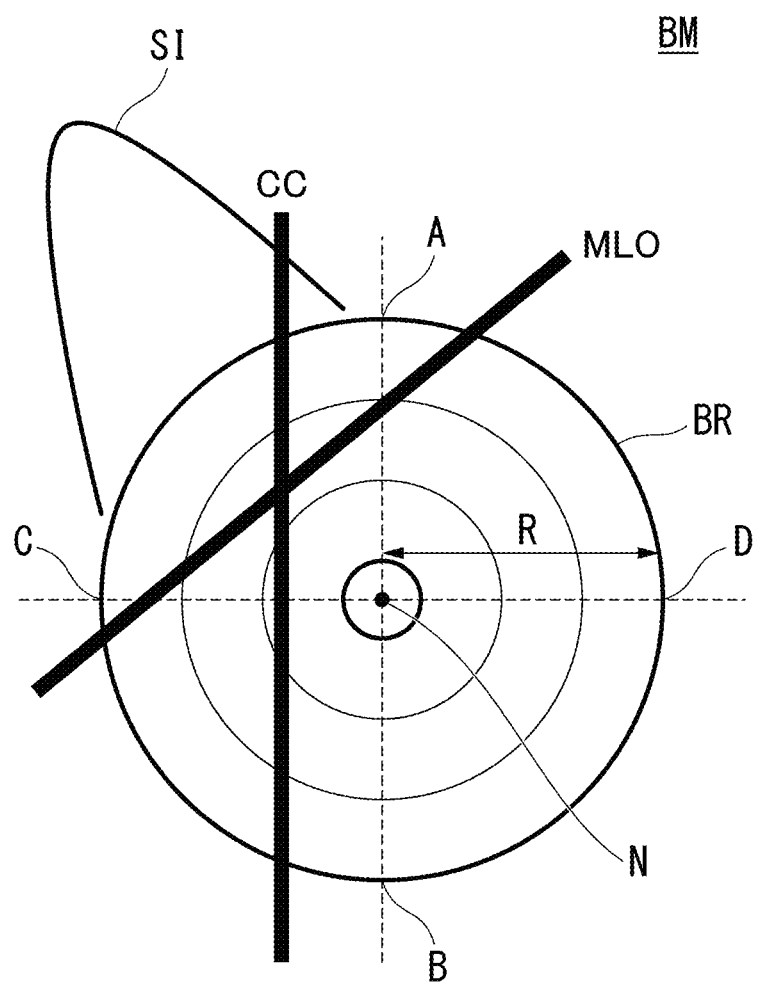
FIG. 7 is a diagram showing a state in which the MLO and CC axes are mapped to the body mark information BM according to the first embodiment.

Next, the transformation function 104 transforms the coordinates of the echo scan guide information ESG into the coordinates of the body mark information BM based on the ratio k. That is, the transformation function 104 multiplies a matrix E of the coordinates of the echo scan guide information ESG by the ratio k according to the following equation (4) to transform all coordinates of the echo scan guide information ESG into coordinates of the body mark information BM, thus mapping the coordinates of the echo scan guide information ESG to the coordinates of the body mark information BM. FIG. 7 is a diagram showing a state in which the MLO and CC axes are mapped to the body mark information BM according to the first embodiment.

$$G=kE \quad (4)$$

Next, the decision function 105 decides imaging positions where an ultrasonic image is to be captured for the body mark information BM to which the MLO and CC axes are mapped (step S106). For example, the decision function 105 decides imaging positions based on input operations received from the operator via the input interface 120. For example, when the operator has input the number of ultrasonic images to be acquired t, the decision function 105 decides t/2 imaging positions for each of the MLO and CC axes on the body mark information BM.

Figure 8:
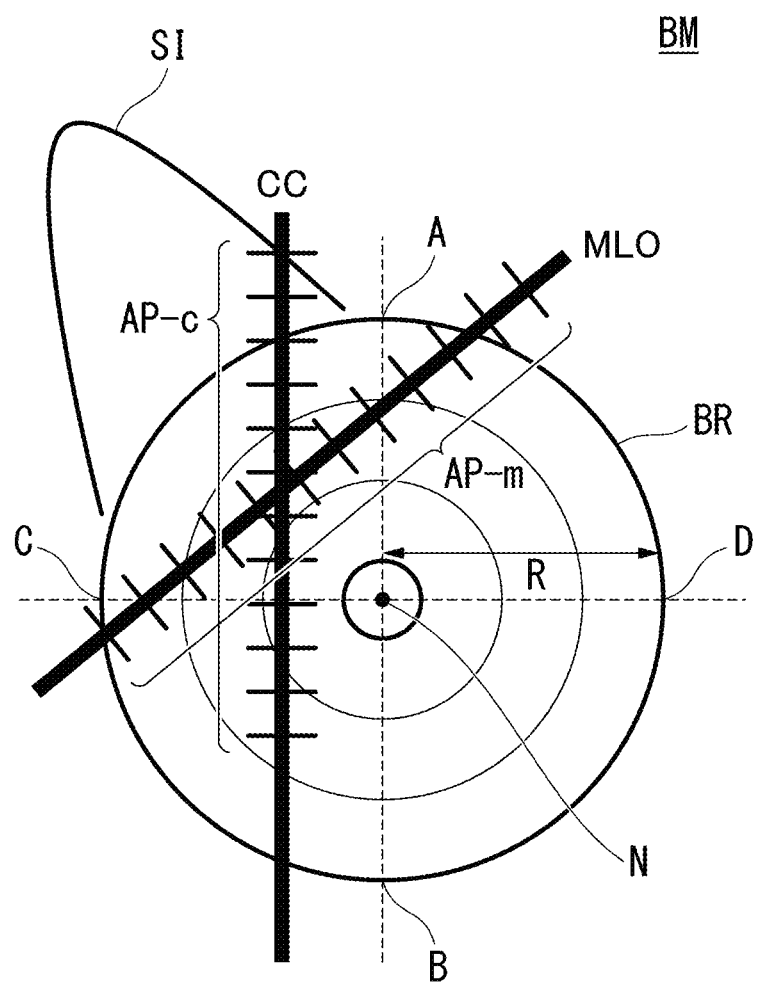
FIG. 8 is a diagram showing a state in which imaging positions are decided for the body mark information BM according to the first embodiment.

FIG. 8 is a diagram showing a state in which imaging positions are decided for the body mark information BM according to the first embodiment. In an example shown in FIG. 8, the operator inputs the number of ultrasonic images to be acquired t=24 and thus the decision function 105 decides 12 imaging positions AP-m that are located on the MLO axis at equal intervals and 12 imaging positions AP-c that are located on the CC axis at equal intervals. A set of the coordinates of the imaging positions AP-m set on the MLO axis is defined as a matrix M and a set of the coordinates of the imaging positions AP-c set on the CC axis is defined as a matrix C.

The decision function 105 may decide the number and locations of imaging positions based on a predetermined guideline. The decision function 105 may decide an axis for setting imaging positions preferentially among the MLO and CC axes based on a predetermined guideline or an input from the operator. After the imaging positions are decided as described above, the operator starts a process of capturing ultrasonic images for the subject using the ultrasound probe 20. For example, the operator scans the entire area of the breast of the subject using the ultrasound probe 20.

Next, the determination function 106 determines whether or not the current position of the ultrasound probe 20 and an imaging position set on the body mark information BM match during an ultrasound examination (step S108). Specifically, the determination function 106 first calculates the current position of the ultrasound probe 20. Then, the determination function 106 determines whether or not the current position thus calculated and an imaging position match.

Figure 9:
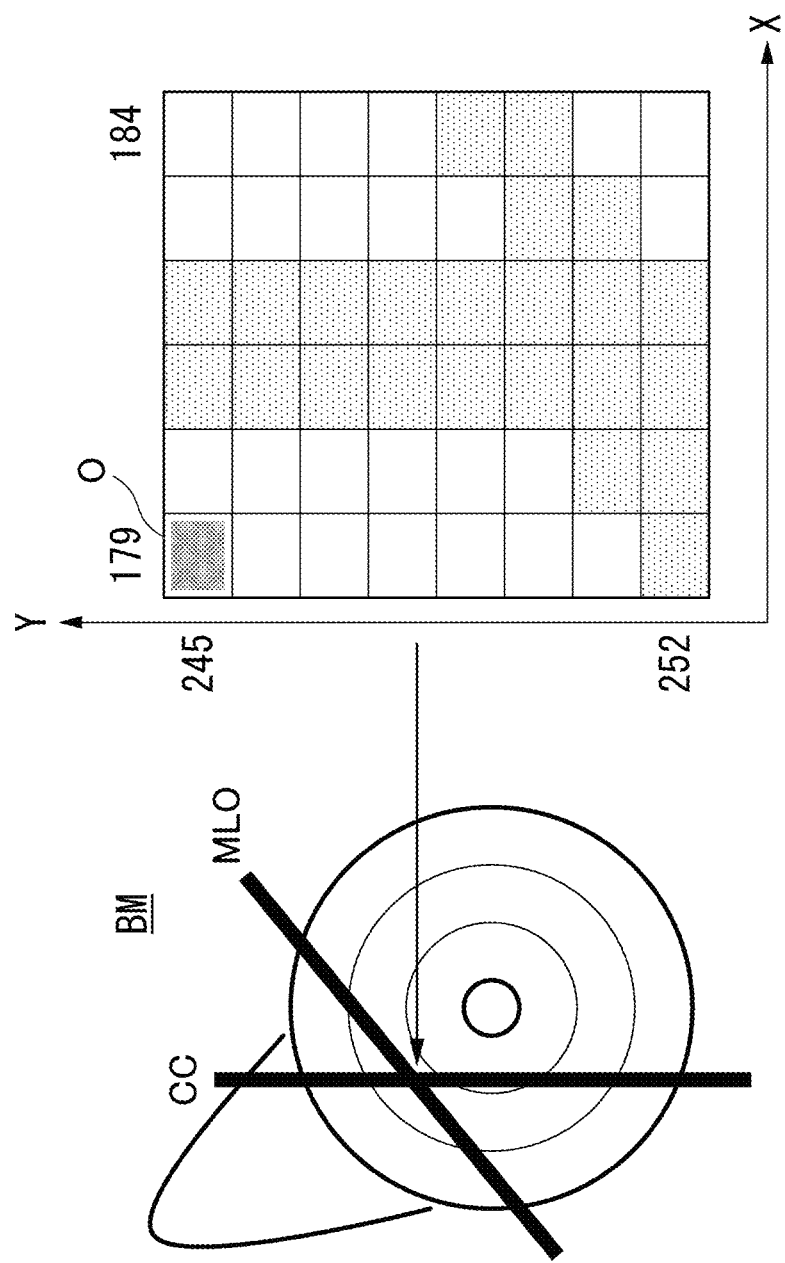
FIG. 9 is a diagram illustrating a determination process performed by a determination function 106 according to the first embodiment.

FIG. 9 is a diagram illustrating a determination process performed by the determination function 106 according to the first embodiment. The current position of the ultrasound probe 20 (a center point of the ultrasound probe 20) shown in the body mark information BM is denoted by O. The determination function 106 continuously determines whether or not (the coordinate position of) the current position O of the ultrasound probe 20 matches (the coordinate position of) any of the imaging positions set on the MLO axis and the imaging positions set on the CC axis. For example, the determination function 106 stores the matrix M and the matrix C in a main storage device of the ultrasonic diagnostic device 1 in advance and compares the current position O of the ultrasound probe 20 and each element of the matrix M and the matrix C one by one. Upon determining that the current position O of the ultrasound probe 20 and an imaging position match, the determination function 106 causes the memory 140 to store an ultrasonic image UT generated by the image generation function 103 in association with subject information, imaging conditions, and the like (step S110). On the other hand, upon determining that the current position O of the ultrasound probe 20 and an imaging position do not match, the determination function 106 does not store the ultrasonic image in the memory 140.

The acquisition function 101 may further acquire a mammography image corresponding to the region of interest from the mammography device 3 or the medical image storage device 7 (an external device) when the determination function 106 has determined that a position in the region of interest matches the examination position.

Figure 10:
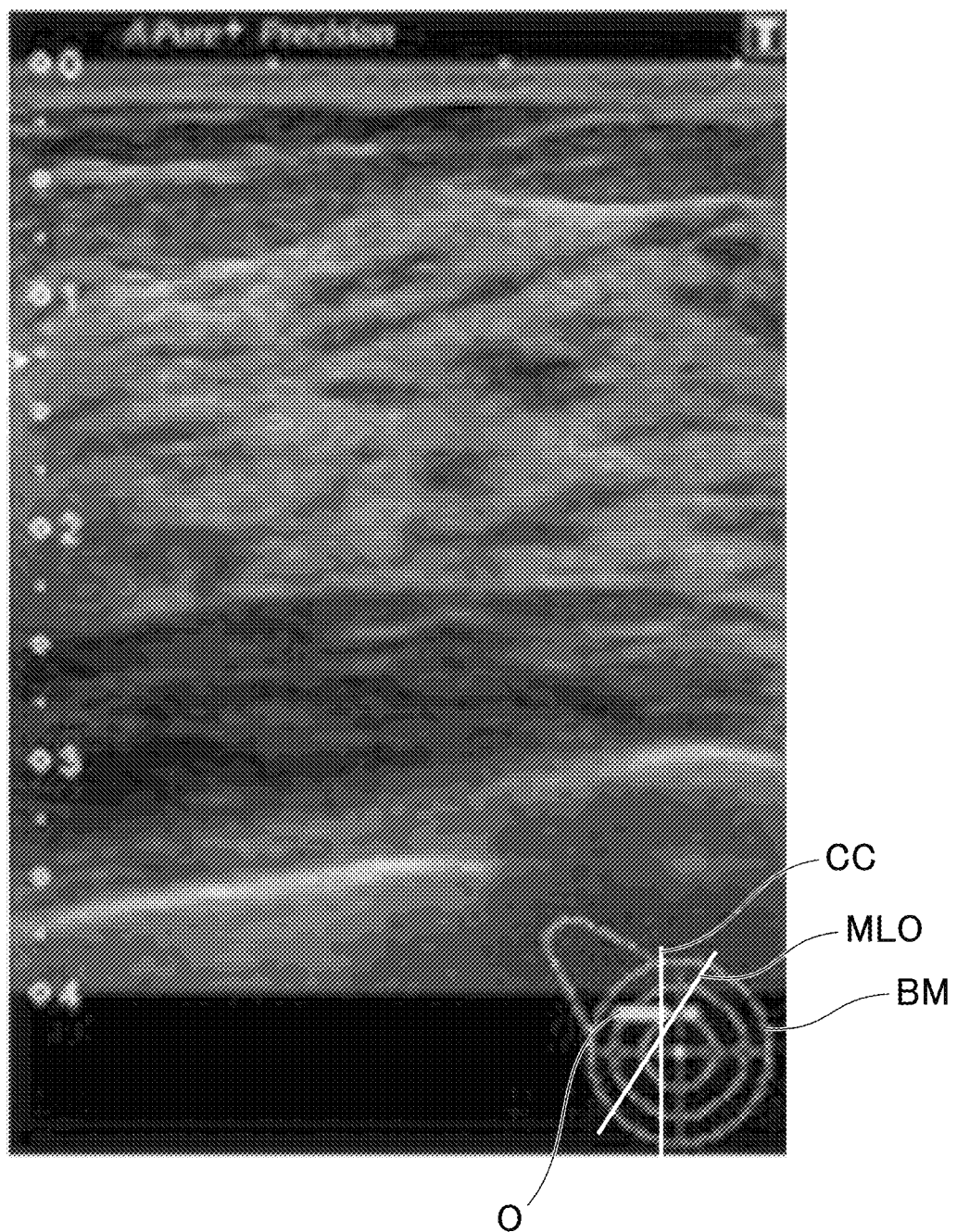
FIG. 10 is a diagram showing an example of an acquisition screen for acquiring an ultrasonic image US according to the first embodiment.

FIG. 10 is a diagram showing an example of an acquisition screen for acquiring an ultrasonic image US displayed on the display 130 during an ultrasound examination according to the first embodiment. In addition to the ultrasonic image US, the body mark information BM to which the MLO and CC axes are mapped is displayed on this acquisition screen. The operator can scan the breast of the subject while checking such a screen to check the positional relationship between the current position O of the ultrasound probe 20 and the imaging positions.

Next, the determination function 106 determines whether or not the acquisition of ultrasonic images for all of the imaging positions set on the MLO axis and the imaging positions set on the CC axis has been completed (step S112). Upon determining that the acquisition of ultrasonic images for all imaging positions has not been completed, the determination function 106 returns to step S108 above to again determine whether or not the current position O of the ultrasound probe 20 and an imaging position match and repeats the subsequent processing.

On the other hand, when the determination function 106 has determined that the acquisition of ultrasonic images for all imaging positions has been completed, the display control function 107 causes the display 130 to display a completion screen indicating that the acquisition of ultrasonic images for all imaging positions has been completed (step S114). By checking the completion screen displayed on the display 130, the operator can confirm that the acquisition of ultrasonic images for all imaging positions has been completed.

Figure 11:
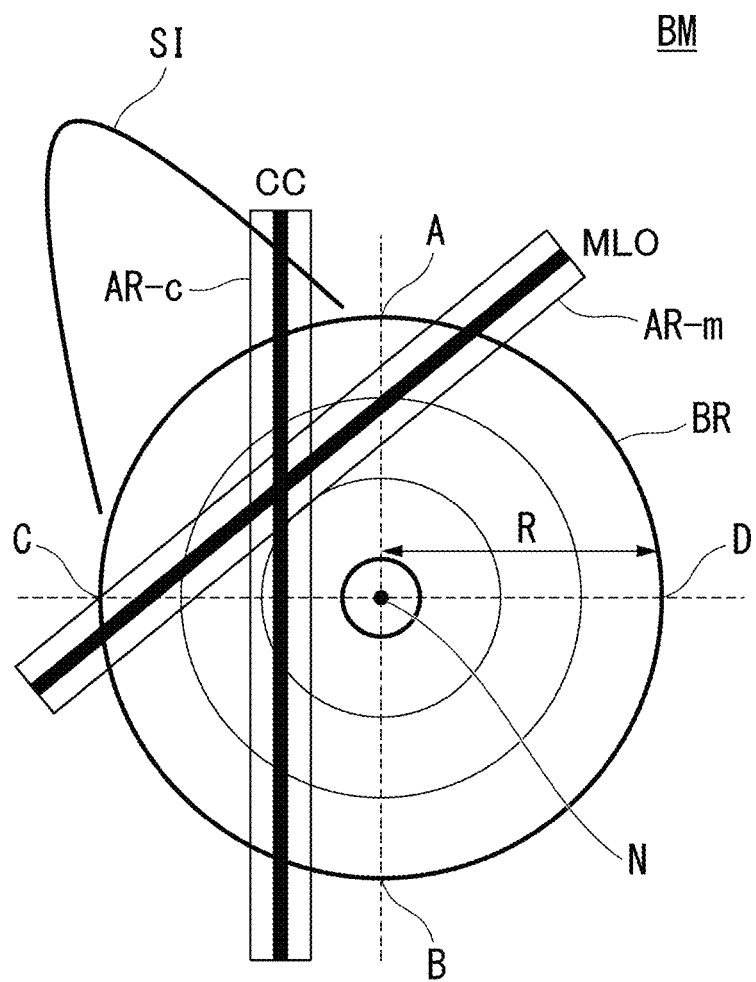
FIG. 11 is a diagram showing how the error ranges of imaging positions are set on the body mark information BM according to the first embodiment.

Ultrasonic images for respective error ranges of the imaging positions set on the MLO axis and the imaging positions set on the CC axis in addition to ultrasonic images for the imaging positions set on the MLO axis and the imaging positions set on the CC axis may also be acquired. The error ranges are set, for example, based on an average error of an ultrasound probe or coordinate transformation. Alternatively, the error ranges may be set, for example, based on an input operation received from the operator via the input interface 120. FIG. 11 is a diagram showing how the error ranges of imaging positions are set on the body mark information BM according to the first embodiment. As shown in FIG. 11, an error range AR-m is set for the MLO axis and an error range AR-c is set for the CC axis.

For example, letting e be an error value, calculations according to the following equations (5) and (6) are performed for each element of the matrices M and C. $M_e$ and $C_e$ are matrices M and C, each containing an error. Matrices E are n matrices with values increasing or decreasing by a smallest unit (for example, 1), starting from 0 and ending with the error. The determination function 106 performs the above determination process on each of the n matrices $M_e$ and the n matrices $C_e$.

$$M_{e,1} = M_1 \pm E_1$$
$$\cdot$$
$$\cdot$$
$$\cdot$$
$$M_{e,n} = M_n \pm E_n \quad (5)$$

$$C_{e,1} = C_1 \pm E_1$$
$$\cdot$$
$$\cdot$$
$$\cdot$$
$$C_{e,n} = C_n \pm E_n \quad (6)$$

Next, the output function 108 outputs the ultrasonic images UI stored in the memory 140 to the terminal device 5 via the network NW, for example, based on an input operation received from the operator via the input interface 120 (step S116). The output function 108 outputs the ultrasonic images UI to the terminal device 5 in a format such as, for example, BMP, JPEG, or DICOM. The output function 108 may also output the ultrasonic images UI to the terminal device 5 in the format of a moving image that consecutively displays the ultrasonic images UI. The output function 108 may also output the ultrasonic images UI to the medical image storage device 7, the CAD device 8, a printing device (not shown), or a portable storage medium (not shown) such as a DVD or a USB. With the above, the process of this flowchart is completed.

According to the first embodiment described above, the labor required to collect ultrasonic images can be reduced. Ultrasonic images corresponding to echo scan guide information are automatically captured and stored by the operator of the ultrasonic diagnostic device 1 simply pressing the ultrasound probe against the entire breast of the subject. This can simplify the process of capturing ultrasonic images, reduce the labor, and shorten the examination time. Further, a doctor or the like who makes a diagnosis using the ultrasonic images thus captured can reduce the effort for searching for a target ultrasonic image suitable for the diagnosis and can shorten the diagnosis time. The doctor can also reduce the risk of missing important ultrasonic images.

Second Embodiment

Hereinafter, a second embodiment will be described. In the first embodiment described above, it has been described that the ultrasonic diagnostic device 1 limits ultrasonic images to be captured and provides them to the terminal device 5 or the like through real-time processing during an ultrasound examination. On the other hand, in the second embodiment, a medical image processing device selects ultrasonic images from all ultrasonic images captured by the ultrasonic diagnostic device 1 after the ultrasound examination has been performed and provides them to the terminal device 5 or the like. In the following description, differences from the first embodiment will be mainly described and elements common to the first embodiment will be omitted. In the description of the second embodiment, the same components as those of the first embodiment will be described with the same reference numerals.

Figure 12:
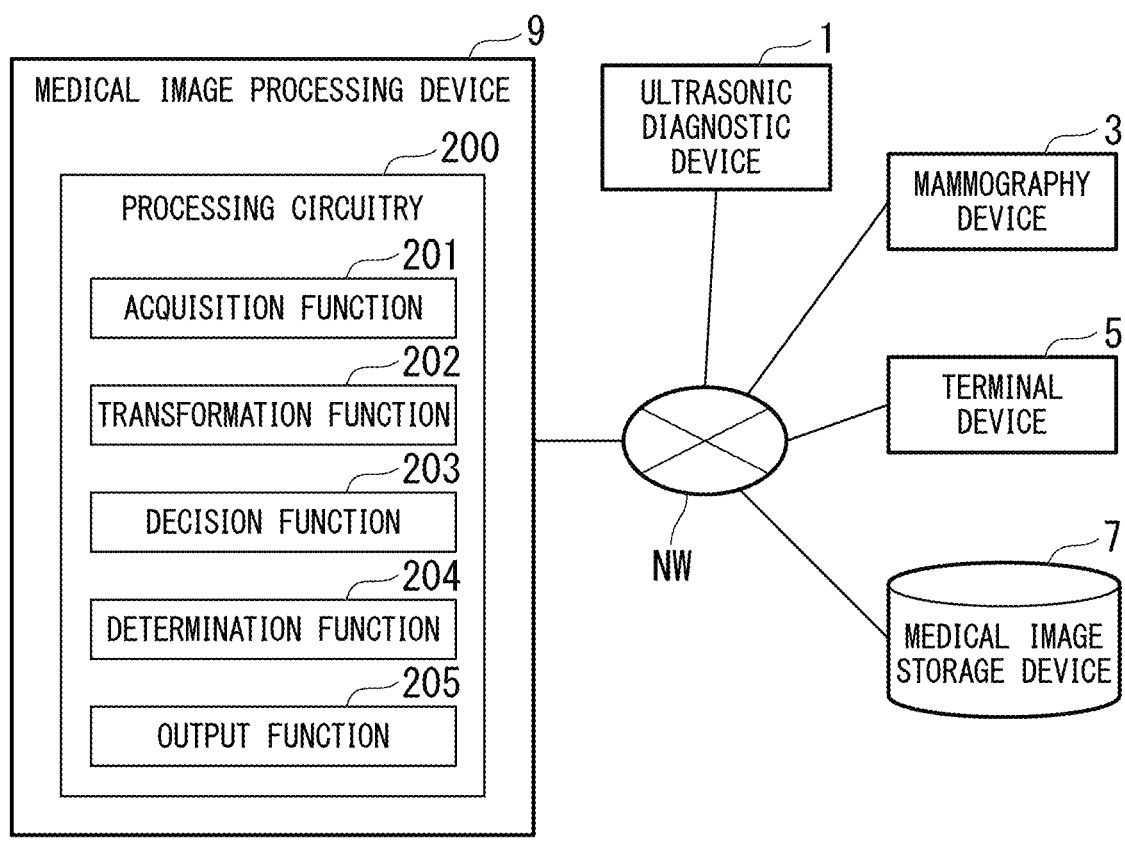
FIG. 12 is a block diagram showing an exemplary configuration of a medical image processing device 9 according to a second embodiment.

FIG. 12 is a block diagram showing an exemplary configuration of a medical image processing device 9 according to the second embodiment. The medical image processing device 9 is connected to an ultrasonic diagnostic device 1, a mammography device 3, a terminal device 5, and a medical image storage device 7 via a network NW such that the medical image processing device 9 can transmit and receive data to and from each of them. The functions of the medical image processing device 9 may be incorporated into the terminal device 5. The medical image processing device 9 is an example of the "medical image processing device."

The medical image processing device 9 includes, for example, processing circuitry 200. The processing circuitry 200 includes, for example, an acquisition function 201, a transformation function 202, a decision function 203, a determination function 204, and an output function 205. The acquisition function 201 is an example of the "acquisition unit." The transformation function 202 is an example of the "transformation unit." The decision function 203 is an example of the "decision unit." The determination function 204 is an example of the "determination unit." The output function 205 is an example of the "output unit."

The acquisition function 201 acquires ultrasonic images, for example, from the ultrasonic diagnostic device 1 or the medical image storage device 7. The acquisition function 201 also acquires echo scan guide information ESG, for example, from the ultrasonic diagnostic device 1, the mammography device 3, or the medical image storage device 7.

The transformation function 202 is equivalent to the transformation function 104 of the ultrasonic diagnostic device 1 described above. That is, the transformation function 202 performs position transformation such that the coordinates of the echo scan guide information ESG acquired by the acquisition function 201 and the coordinates of body mark information associated with an ultrasonic image are represented in the same coordinate plane.

The decision function 203 is equivalent to the decision function 105 of the ultrasonic diagnostic device 1 described above. That is, the decision function 203 decides positions on the body of the subject where an ultrasonic image is to be acquired (hereinafter referred to as "acquisition positions"), for example, based on input operations received from the operator via an input interface (not shown) of the medical image processing device 9. The decision function 105 may also decide the number and locations of acquisition positions based on a predetermined guideline.

The determination function 204 is equivalent to the determination function 106 of the ultrasonic diagnostic device 1 described above. That is, the determination function 204 determines whether or not the position of the ultrasound probe 20 indicated by the coordinates of the body mark information and a decided acquisition position match. Upon determining that the position of the ultrasound probe 20 and a decided acquisition position match, the determination function 204 extracts an ultrasonic image corresponding to the decided acquisition position as an output target. That is, the determination function 204 determines whether or not a position in the region of interest matches an examination position on the body of the subject associated with an ultrasonic image that has been captured.

The output function 205 is equivalent to the output function 108 of the ultrasonic diagnostic device 1 described above. That is, the output function 205 outputs the extracted ultrasonic images to the terminal device 5 via the network NW, for example, based on an input operation received from the operator via the input interface (not shown) of the medical image processing device 9.

According to the second embodiment described above, ultrasonic images corresponding to the echo scan guide information are automatically extracted and output. This can reduce the labor required to collect ultrasonic images.

Third Embodiment

Hereinafter, a third embodiment will be described. In the first embodiment described above, it has been described that ultrasonic images for the imaging positions set on the MLO axis and the imaging positions set on the CC axis are provided to the terminal device 5 or the like. On the other hand, in the third embodiment, only an ultrasonic image corresponding to a position where the MLO and CC axes intersect is extracted and provided to the terminal device 5 or the like. In the following description, differences from the first embodiment will be mainly described and points common to the first embodiment will be omitted. In the description of the third embodiment, the same components as those of the first embodiment will be described with the same reference numerals.

The output function 108 extracts an ultrasonic image UI corresponding to the position where the MLO and CC axes intersect from ultrasonic images UT stored in the memory 140, for example, based on an input operation received from the operator via the input interface 120. The output function 108 outputs the extracted ultrasonic image UI to the terminal device 5 via the network NW. That is, the output function 108 outputs an ultrasonic image corresponding to an overlapping region of the first region of interest (the MLO axis) and the second region of interest (the CC axis) from among the saved ultrasonic images.

Figure 13:
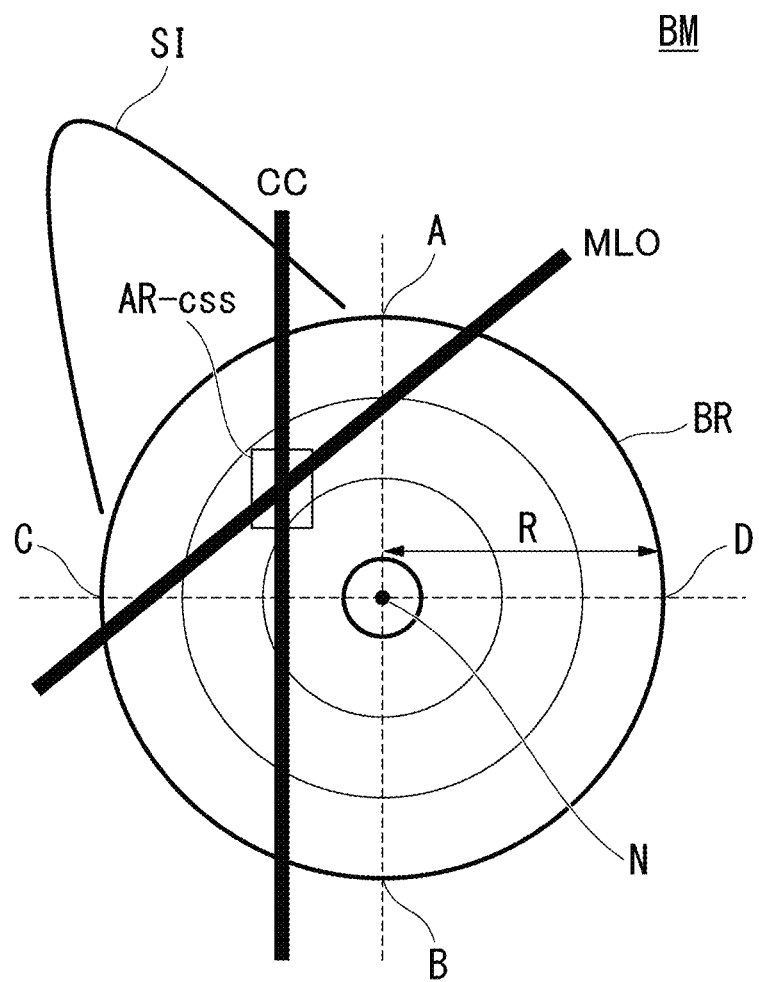
FIG. 13 is a diagram showing an intersection position AR-css where MLO and CC axes intersect on body mark information BM according to a third embodiment.

FIG. 13 is a diagram showing an intersection position AR-css where the MLO and CC axes intersect on the body mark information BM according to the third embodiment. The output function 108 extracts an ultrasonic image corresponding to such an intersection position AR-css as a representative ultrasonic image and outputs it to the terminal device 5. For example, the output function 108 refers to information on imaging positions associated with the ultrasonic images UI in the memory 140 and extracts a pair of elements whose coordinate positions match (which may include a predetermined error range) from elements included in the matrix M and elements included in the matrix C and then extracts an ultrasonic image corresponding to the extracted pair of elements.

The output function 108 may also assign label information to an ultrasonic image corresponding to the intersection position AR-css and output the ultrasonic image to the terminal device 5 together with other ultrasonic images. Also, rather than the output function 108 extracting only an ultrasonic image corresponding to the intersection position AR-css, the determination function 106 may determine whether or not the current position O of the ultrasound probe 20 and the intersection position AR-css match and store a corresponding ultrasonic image UI in the memory 140 only when they match.

According to the third embodiment described above, only an ultrasonic image corresponding to the intersection position AR-css is extracted as a representative ultrasonic image and output to the terminal device 5, such that a doctor who makes a diagnosis can reduce the number of ultrasonic images to be checked and can further shorten the diagnosis time.

Fourth Embodiment

Hereinafter, a fourth embodiment will be described. In the first embodiment described above, it has been described that ultrasonic images for imaging positions set on a pair of MLO and CC axes that target a certain lesion site are provided to a terminal device 5 or the like. On the other hand, in the fourth embodiment, ultrasonic images for imaging positions set on a plurality of pairs of MLO axes and CC axes that target a plurality of lesion sites are provided to the terminal device 5 or the like. In the following description, differences from the first embodiment will be mainly described and points common to the first embodiment will be omitted. In the description of the fourth embodiment, the same components as those of the first embodiment will be described with the same reference numerals.

Figure 14:
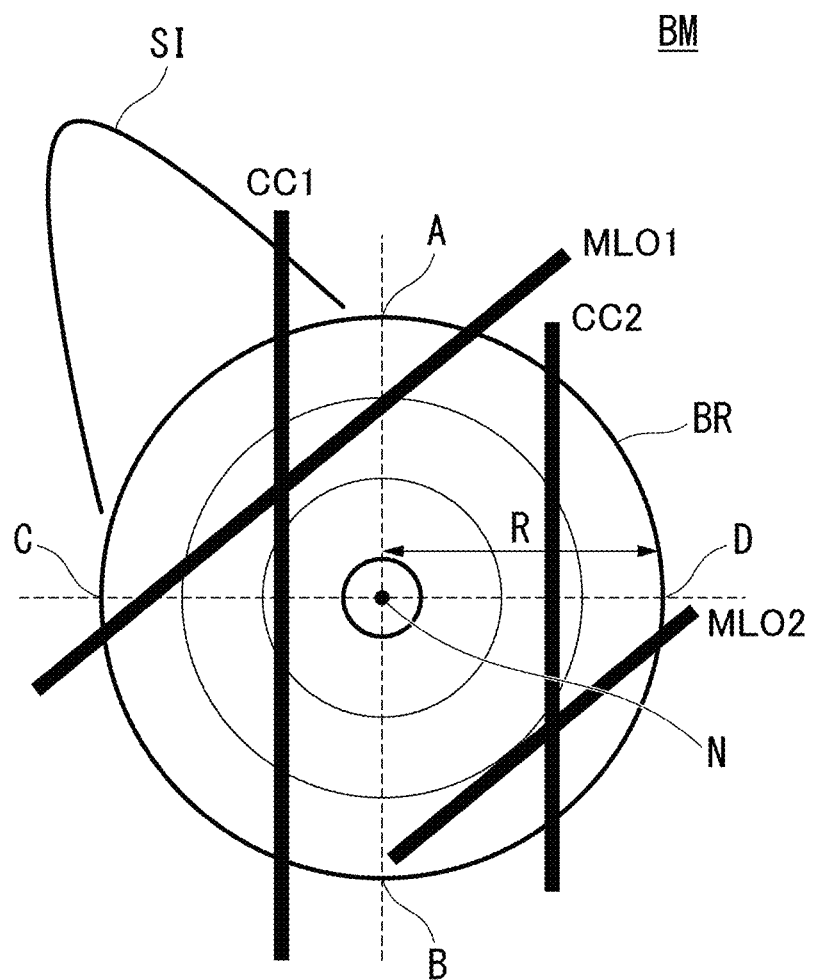
FIG. 14 is a diagram showing a state in which a plurality of pairs of MLO axes and CC axes are mapped to body mark information BM according to a fourth embodiment.

FIG. 14 is a diagram showing a state in which a plurality of pairs of MLO axes and CC axes are mapped to body mark information BM according to the fourth embodiment. In an example shown in FIG. 14, a pair of MLO1 and CC1 axes corresponding to a first lesion site and a pair of MLO2 and CC2 axes corresponding to a second lesion site are mapped to the body mark information BM. The determination function 106 determines whether or not the current position of the ultrasound probe 20 matches an imaging position set on such MLO and CC axes corresponding to the plurality of lesion sites during an ultrasound examination, such that it is possible to collect ultrasonic images corresponding to a plurality of lesion sites together. That is, the region of interest includes a plurality of regions of interest corresponding to a plurality of lesion sites. Upon determining that a position in the plurality of regions of interest matches an examination position, the determination function 106 saves or outputs an ultrasonic image corresponding to the examination position.

According to the fourth embodiment described above, ultrasonic images corresponding to a plurality of lesion sites can be collected together and the labor required to collect ultrasonic images can be reduced.

Fifth Embodiment

Hereinafter, a fifth embodiment will be described. In the first embodiment described above, it has been described that the ultrasonic images UI stored in the memory 140 are provided to the terminal device 5 or the like. On the other hand, in the fifth embodiment, an ultrasonic image(s) in which a lesion has been detected by the CAD device 8 (the ultrasonic CAD device) is extracted from the ultrasonic images UI stored in the memory 140 as a representative ultrasonic image(s) and provided to a terminal device 5 or the like. In the following description, differences from the first embodiment will be mainly described and points common to the first embodiment will be omitted. In the description of the fifth embodiment, the same components as those of the first embodiment will be described with the same reference numerals.

The CAD device 8 (the ultrasonic CAD device) acquires captured ultrasonic images UI from the ultrasonic diagnostic device 1 or the medical image storage device 7. The CAD device 8 uses the coordinates of the body mark information to extract an ultrasonic image(s) in which a lesion has been detected from the ultrasonic images UI as a representative image(s) and transmits the extracted ultrasonic image(s) to the ultrasonic diagnostic device 1. The output function 108 of the ultrasonic diagnostic device 1 provides the ultrasonic image(s) thus extracted by the CAD device 8 to the terminal device 5 or the like. The output function 108 may assign label information to the ultrasonic image(s) extracted by the CAD device 8 and output the ultrasonic image(s) to the terminal device 5 together with other ultrasonic images. That is, the output function 108 outputs an ultrasonic image(s) in which a lesion site has been detected by a computer-aided diagnostic device from among the saved ultrasonic images.

According to the fifth embodiment described above, only an ultrasonic image(s) extracted by the CAD device 8 is output to the terminal device 5, such that the doctor who makes a diagnosis can reduce the number of ultrasonic images to be checked and can further shorten the diagnosis time.

Sixth Embodiment

Hereinafter, a sixth embodiment will be described. In the first embodiment described above, it has been described that the operator manually operates the ultrasound probe 20 to perform an ultrasound examination. On the other hand, in the sixth embodiment, an ultrasonic diagnostic device that performs an automatic scan is used. In the following description, differences from the first embodiment will be mainly described and points common to the first embodiment will be omitted. In the description of the sixth embodiment, the same components as those of the first embodiment will be described with the same reference numerals.

The ultrasonic diagnostic device 1 stores (a collection of) ultrasonic images of the entire breast of the subject in the memory 140 in association with body mark information BM based on automatic scan control. For example, based on an input operation received from the operator via the input interface 120, the output function 108 extracts ultrasonic images corresponding to imaging positions from the ultrasonic images stored in the memory 140 by referring to body mark information BM associated with the ultrasonic images (where transformation into body mark coordinates using human body coordinates can alternatively be applied) and outputs the extracted ultrasonic images to the terminal device 5. That is, the output function 108 outputs ultrasonic images associated with examination positions of the subject which match positions in the region of interest from among ultrasonic images captured based on the automatic scan control.

According to the sixth embodiment described above, even when an ultrasonic diagnostic device that performs an automatic scan is used, only ultrasonic images corresponding to imaging positions can be output to the terminal device 5, such that the labor required to collect ultrasonic images can be reduced.

Seventh Embodiment

Hereinafter, a seventh embodiment will be described. In the first embodiment described above, it has been described that echo scan guide information ESG set by a technician, a doctor (a radiologist), or the like who has performed a mammography examination is used. On the other hand, in the seventh embodiment, echo scan guide information ESG generated from a result of analysis by the CAD device 8 (the mammography CAD device) is used. In the following description, differences from the first embodiment will be mainly described and points common to the first embodiment will be omitted. In the description of the seventh embodiment, the same components as those of the first embodiment will be described with the same reference numerals. The acquisition function 101 acquires the echo scan guide information ESG generated from the result of analysis by the CAD device 8 (the mammography CAD device). The transformation function 104, the decision function 105, and the determination function 106 perform the various processing described above using the echo scan guide information ESG acquired from the CAD device 8.

According to the seventh embodiment described above, echo scan guide information ESG generated from a result of analysis by the CAD device 8 is used, such that a technician, a doctor (a radiologist), or the like who has performed a mammography examination does not need to generate echo scan guide information ESG and the examination procedure can be simplified.

At least one embodiment described above includes a transformation unit (104, 202) that performs position transformation such that a position in a region of interest set in a captured mammography image of a breast of a subject and an examination position on a body of the subject in an ultrasound examination are represented in a plane of the same scale and a determination unit (106, 204) that determines whether or not the position in the region of interest and the examination position match in the plane, wherein the determination unit (106, 204) saves or outputs an ultrasonic image corresponding to the examination position upon determining that the position in the region of interest and the examination position match, whereby the labor required to collect ultrasonic images can be reduced.

The embodiments described above can be expressed as follows.

A medical image processing device including processing circuitry,
wherein the processing circuitry is configured to:
perform position transformation to represent a position in a region of interest set in a captured mammography image of a breast of a subject and an examination position on a body of the subject in an ultrasound examination in a plane of the same scale;
determine whether or not the position in the region of interest and the examination position match in the plane; and
save or output an ultrasonic image corresponding to the examination position upon determining that the position in the region of interest matches the examination position.

Although some embodiments have been described, these embodiments have been presented by way of example and are not intended to limit the scope of the invention. These embodiments can be implemented in various other forms, and various omissions, substitutions, and changes can be made without departing from the spirit of the invention. These embodiments and modifications thereof are included in the scope or spirit of the invention as well as in the scope of the invention described in the claims and their equivalents.

What is claimed is:

1. A medical image processing device comprising:
processing circuitry configured to:
perform position transformation to represent a position in a region of interest set in a mammography image of a breast of a subject captured by a mammography device and an examination position on a body of the subject in an ultrasound examination by an ultrasonic diagnostic device in a plane of the same scale, to generate body mark information to which the position in the region of interest is mapped, the body mark information indicating the examination position which is in contact with an ultrasound probe during the ultrasound examination;
decide an acquisition position of an ultrasonic image in the region of interest on the body mark information; and
determine whether or not the decided acquisition position and the examination position match in the body mark information,
wherein the processing circuitry is configured to save or output an ultrasonic image corresponding to the examination position upon determining that the decided acquisition position matches the examination position, and
wherein the processing circuitry is configured to perform the position transformation based on a ratio of a first distance to a second distance, the first distance being a distance between a position of a nipple of the breast and an end point of the breast on the body mark information, the second distance being a distance between a position of a nipple of the breast and an end point of the breast on echo scan guide information indicating the region of interest set for the mammography image.

2. The medical image processing device according to claim 1, wherein the region of interest includes a first region of interest set in a first mammography image of the breast captured in a first direction and a second region of interest set in a second mammography image of the breast captured in a second direction, and
the processing circuitry is configured to decide the acquisition position within the first region of interest and the second region of interest.

3. The medical image processing device according to claim 1, wherein the processing circuitry is configured to determine whether or not the decided acquisition position matches an examination position on the body of the subject associated with an ultrasonic image that has been captured.

4. The medical image processing device according to claim 1, further comprising a computer-aided diagnostic device configured to automatically detect a lesion site from the mammography image and set the region of interest including the detected lesion site.

5. The medical image processing device according to claim 1, wherein the processing circuitry is configured to acquire information on the region of interest from an external device.

6. The medical image processing device according to claim 1, wherein the processing circuitry is configured to perform setting for identifying the examination position on the body of the subject, which is in contact with the ultrasound probe during the ultrasound examination, based on position information of a predetermined portion on the body of the subject.

7. The medical image processing device according to claim 5, wherein the processing circuitry is configured to further acquire a mammography image corresponding to the region of interest from the external device upon determining that the decided acquisition position matches the examination position.

8. The medical image processing device according to claim 2, wherein the processing circuitry is configured to output an ultrasonic image corresponding to an overlapping region of the first region of interest and the second region of interest from among saved ultrasonic images.

9. The medical image processing device according to claim 1, wherein the region of interest includes a plurality of regions of interest corresponding to a plurality of lesion sites, and
the processing circuitry is configured to save or output an ultrasonic image corresponding to the examination position upon determining that the decided acquisition position of the ultrasonic image in the plurality of regions of interest matches the examination position.

10. The medical image processing device according to claim 1, wherein the processing circuitry is configured to output an ultrasonic image in which a lesion site has been detected by a computer-aided diagnostic device from among saved ultrasonic images.

11. The medical image processing device according to claim 1, wherein the processing circuitry is configured to output an ultrasonic image associated with an examination position of the subject which matches the decided acquisition position from among ultrasonic images captured based on automatic scan control.

12. An ultrasonic diagnostic device comprising the medical image processing device according to claim 1.

13. The medical image processing device according to claim 1, wherein the region of interest includes a first region of interest set in a first mammography image of the breast captured in a first direction and a second region of interest set in a second mammography image of the breast captured in a second direction, and
the processing circuitry is configured to decide acquisition positions corresponding to a number of ultrasonic images to be acquired, for the first region of interest and the second interest, the number of ultrasonic images to be acquired being input by an operator.

14. A computer-readable non-transient storage medium that stores a program causing a computer for a medical image processing device to:
perform position transformation to represent a position in a region of interest set in a mammography image of a breast of a subject captured by a mammography device and an examination position on a body of the subject in an ultrasound examination by an ultrasonic diagnostic device in a plane of the same scale, to generate body mark information to which the position in the region of interest is mapped, the body mark information indicating the examination position which is in contact with an ultrasound probe during the ultrasound examination;
decide an acquisition position of an ultrasonic image in the region of interest on the body mark information;
determine whether or not the decided acquisition position and the examination position match in the body mark information; and
save or output an ultrasonic image corresponding to the examination position upon determining that the decided acquisition position matches the examination position,
wherein the position transformation is performed based on a ratio of a first distance to a second distance, the first distance being a distance between a position of a nipple of the breast and an end point of the breast on the body mark information, the second distance being a distance between a position of a nipple of the breast and an end point of the breast on echo scan guide information indicating the region of interest set for the mammography image.

15. The computer-readable non-transient storage medium according to claim 14, wherein the region of interest includes a first region of interest set in a first mammography image of the breast captured in a first direction and a second region of interest set in a second mammography image of the breast captured in a second direction, and the program causes the computer to decide acquisition positions corresponding to a number of ultrasonic images to be acquired, for the first region of interest and the second interest, the number of ultrasonic images to be acquired being input by an operator.

* * * * *